United States Patent [19]

Kauser et al.

[11] Patent Number: 5,773,432
[45] Date of Patent: Jun. 30, 1998

[54] METHOD FOR LOWERING PLASMA LEVELS OF LIPOPROTEIN(A)

[75] Inventors: Katalin Kauser, El Sobrante; Gabor M. Rubanyi, Alamo, both of Calif.

[73] Assignee: Schering Aktiengesellschaft, Berlin, Germany

[21] Appl. No.: 739,840

[22] Filed: Oct. 30, 1996

[51] Int. Cl.$^6$ .................................................. A61K 31/56
[52] U.S. Cl. .......................... 514/182; 514/824; 514/866
[58] Field of Search ................................... 514/182, 824, 514/866

[56] References Cited

U.S. PATENT DOCUMENTS

| | | | |
|---|---|---|---|
| 4,133,814 | 1/1979 | Jones et al. ..................... | 260/326.55 A |
| 4,418,068 | 11/1983 | Jones ........................................ | 424/267 |
| 5,489,611 | 2/1996 | Lee et al. .................................. | 514/557 |
| 5,496,828 | 3/1996 | Cullinan ................................... | 514/324 |
| 5,496,851 | 3/1996 | Grinnell .................................... | 514/443 |

FOREIGN PATENT DOCUMENTS

| | | |
|---|---|---|
| 0605193A1 | 12/1993 | European Pat. Off. . |
| 96/28462 | 9/1996 | WIPO . |

OTHER PUBLICATIONS

Frazer, K. et al., *Nature Genetics* (1995) 9:424–431.
Kim et al., *Arteriosclerosis and Thrombosis* (1994) 14(2):275–281.
Brown et al. *Arteriosclerosis Thromb* (1993).
Anwar et al. (1993) *Nephrol. Dial. Transplant.* 8:71–74.
Heller et al., *Diabetes Care* (1993) 16(5):819–823.
Crook et al.. *Atherosclerosis* (1992) 92:41–47.
Radar et al. *JAMA* (1992) 267(8):1109–1112.
Boerwinkle et al., *J. Clin. Invest.* (1992) 90:52–60.
Lawn et al., *Nature* (1992) 360: 670–672.
Muller et al., *German J. Opthalmol* (1992) 1:338–341.
Tyrell et al., *J. of Int. Medicine*, (1992) 232:349–352.
Kapelrud et al., *Br. Med. J.* (1991) 303:675–678.
Mosca, et al., *Circulation* (1991) 84(4), Suppl II: 2169.
Muesing et al., *Arteriosclerosis Thromb.* (1991) 11(95):1452(a).
Farish et al., *Br. Med J.* (1991) 303:694.
Meilahn et al., *Circulation* (1991) 84(4), Suppl. II: 2170 (abstract).
Srinivasan, et al., *Circulation* (1991) 84(1):160–167.
Scanu et al., *J. Clin. Invest.* (1990) 85:1709–1715.
Bruckert et al., *JAMA* (1990) 263(1):35–36.
Sandkamp et al., *Academic Press, Inc.* (1990) 205–210.
Davis et al., *C.V.D.* (1990) 25 (abstract).
Utermann, *Science* (1989) 246:904–910.
Hajjar et al., *Nature* (1989) 339;303–305.
Harpel et al., *Proc. Natl. Acad. Sci. USA* (1989) 86:3847–3851.
Kraft et al., *J. Clin. Invest.* (1989) 83:137–142.
Tomlinson et al.,*J. Biol. Chem.* (1989) 264(10):5957–5965.
Scanu, *Arch. Pathol. Lab. Med.* (1988) 112:1045–1047.
Hoff et al., *Circulation* (1988) 77:1238–1244.
Karadi et al., *Biochim, Biophys. Acta* (1988) 960:91–97.
McLean et al., *Nature* (1987) 330:132–137.
Rhoades, et al., *JAMA* (1986) 256(18):2540–2544.
Dahleen et al., *Circulation* (1986) 74(4):758–765.
Armstrong et al., *Atherosclerosis* (1986) 62:249–257.
Zechner et al., *Metabolism* (1986) 35:333–336.
Schriewer et al., *J. Clin. Chem. Clin. Biochem.* (1984) 22:591–596.
Albers et al., *Biochim. Biophys. Acta* (1984) 795:293–296.
Kostner, *Atherosclerosis* (1981) 38:51–61.
Krempler et al., *J. Clin. Invest.* (1980) 65:148301490.

*Primary Examiner*—Kimberly Jordan
*Attorney, Agent, or Firm*—Carol J. Roth

[57] ABSTRACT

A method of lowering plasma levels of Lp(a) or inhibiting the generation of apo(a) in a human by administering an effective amount of a compound of formula (I):

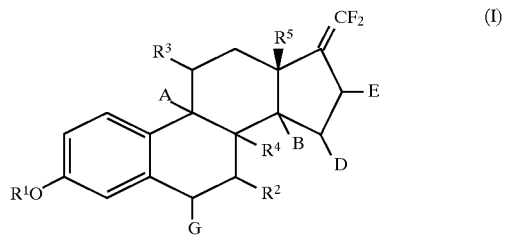

wherein:

$R^1$ is hydrogen or alkyl;

A, B, D, E, G, $R^2$ and $R^3$ each are hydrogen, and $R^4$ is hydrogen in the β-position; or $R^2$ with $R^4$, $R^4$ with A, A with $R^3$, B with D, D with E, or G with $R^2$ is a bond, and the other substituents are each hydrogen; or $R^2$ is alkyl in the β-position and A, B, D, E, G, $R^3$ and $R^4$ are each hydrogen; or $R^3$ is alkoxy in the β-position and A, B, D, E, G, $R^2$ and $R^4$ are each hydrogen; or $R^4$ is hydrogen in the α-position and A, B, D, E, G, $R^2$ and $R^3$ are each hydrogen; and $R^5$ is methyl or ethyl, is disclosed.

22 Claims, 1 Drawing Sheet

Plasma levels of apo(a) in treated and control mice after 2-week treatment.

Values represent means±SEM of plasma apo(a) levels (left Y axis) and uterine weight (right Y axis) measured in 3 mice in each group.

Asterisk (*) indicates statistically significant ($p<0.05$) difference between the treated and control group.

METHOD FOR LOWERING PLASMA LEVELS OF LIPOPROTEIN(A)

FIELD OF THE INVENTION

This invention is directed to a method for lowering plasma levels of lipoprotein(a) in humans. In particular, this invention is directed to the use of certain 17-difluoromethylene-estratrienes to lower plasma levels of lipoprotein(a) in humans, thereby being useful in the treatment and prevention of premature occlusive arterial disease.

BACKGROUND OF THE INVENTION

Lipoprotein(a) (Lp(a)) is an unique lipoprotein found in the plasma of only human, some sub-human primates and the European hedgehog. Lp(a) is considered an independent risk factor for premature occlusive arterial diseases, such as atherosclerosis, coronary artery disease, myocardial infarction, cerebral infarction (stroke), peripheral artery disease and restenosis following balloon angioplasty. The structure of Lp(a) is closely related to LDL in that it consists of LDL with an additional disulfide-linked apolipoprotein, apo (a). Apo(a) is covalently bound to the glycoprotein Apo B100, an integral part of LDL. Apo B100 allows the LDL molecule to carry the hydrophobic cholesterol in the plasma and tissue fluids. In contrast, apo(a) is water soluble and does not bind lipid. The major site of synthesis of plasma apo(a) appears to be the liver. However, it is currently unknown where Lp(a) is assembled. LDL and apo(a) may be secreted independently of each other, and the assembly may take place in the plasma. Such a mechanism could explain why only a fraction of LDL, which varies from subject to subject, is complexed with apo(a). This fraction is determined by the amount of apo(a) secreted rather than by the LDL concentration in plasma. From in vivo turnover studies of Lp(a) in humans, it has been concluded that differences in plasma Lp(a) concentrations among individuals are a result of differences in synthesis rather than differences in catabolism of Lp(a).

Elevated plasma levels of Lp(a) is associated with premature occlusive arterial disease, such as coronary heart disease (CHD) and stroke. In addition, the association between concentrations of Lp(a) in serum and coronary artery disease (CAD) has been shown. Furthermore, the level of Lp(a) in the plasma has been shown to independently correlate with the rate of restenosis (after balloon angioplasty), peripheral arterial occlusive disease, diabetic vasculopathies in Type II diabetes mellitus, increased CHD risk in patients undergoing continuous ambulatory peritoneal dialysis, and stenosis of bypass grafts.

Surprisingly, the associations of Lp(a) with other known risk factors for CHD, for example, plasma lipid (triglycerides, LDL, HDL) levels, dietary fat intake, hypertension, diabetes, overweight and cigarette smoking, have been consistently weak or absent and do not appear to explain the relation of Lp(a) to CHD.

It is widely believed that the level of Lp(a) in the plasma is under strong genetic control, with non-genetic factors, including gender, diabetes mellitus and end-stage renal disease, having some influence. Lp(a) levels in men and women differ significantly and are influenced by physiological conditions such as puberty and menopause when production of sex hormones is altered. Lp(a) levels in females continue to rise with age, particularly in the premenopausal years, while in males they plateau at about 25 years of age. In addition, Lp(a) plasma levels have been found to be higher in postmenopausal then premenopausal women of comparable age. A gender related difference can also be observed in studies which have correlated the levels of Lp(a) with the extent of angiographically documented CAD. Lp(a) plasma levels have also been shown to be more predictable of CAD in females than in males.

The use of steroid hormones (e.g., estrogens, progesterone and testosterone) to lower plasma levels of Lp(a) has been shown. For example, Lp(a) plasma concentrations have been shown to be influenced by the administration of anabolic steroids, progesterone, estrogen, and combination of estrogen and progestogen to postmenopausal women. In males affected by prostatic cancer, estrogen therapy lowered Lp(a) plasma levels by 50%, while orchidectomy treatment slightly increased the plasma concentration of Lp(a), suggesting that estrogen and testosterone exert a regulatory role on serum Lp(a) levels in men.

We have now discovered that certain 17-difluoromethylene-estratrienes are effective in inhibiting the generation of apo(a) and are, consequently, effective in lowering plasma levels of Lp(a), and are therefore useful in treating disease-states which are alleviated by inhibiting the generation of apo(a) or by lowering the plasma levels of Lp(a). These compounds have not been disclosed previously as having this ability.

SUMMARY OF THE INVENTION

Accordingly, one aspect of this invention is directed to a method of lowering plasma levels of Lp(a) in a human, which method comprises administering to a human in need thereof an effective amount of a compound of formula (I):

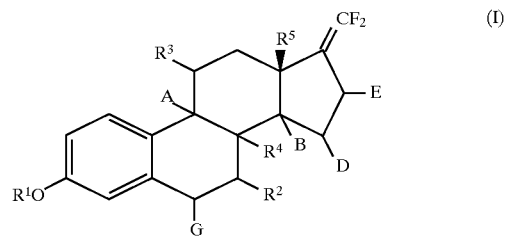

wherein:

$R^1$ is hydrogen or alkyl;

A, B, D, E, G, $R^2$ and $R^3$ each are hydrogen, and $R^4$ is hydrogen in the β-position; or $R^2$ with $R^4$, $R^4$ with A, A with $R^3$, B with D, D with E, or G with $R^2$ is a bond, and the other substituents are each hydrogen; or $R^2$ is alkyl in the β-position and A, B, D, E, G, $R^3$ and $R^4$ are each hydrogen; or $R^3$ is alkoxy in the β-position and A, B, D, E, G, $R^2$ and $R^4$ are each hydrogen; or $R^4$ is hydrogen in the α-position and A, B, D, E, G, $R^2$ and $R^3$ are each hydrogen; and $R^5$ is methyl or ethyl.

A further aspect of this invention is directed to a method of inhibiting the generation of apo(a) in a human, which method comprises administering a human in need thereof an effective amount of a compound of formula (I) as defined above.

Another aspect of this invention is directed to a method of treating a human having a disease-state which is alleviated by reducing the plasma levels of Lp(a), which method comprises administering to the human in need thereof a therapeutically effective amount of a compound of formula (I) as defined above.

A further aspect of this invention is directed to a method of treating a human having a disease-state which is alleviated by inhibiting the generation of apo(a), which method comprises administering to the human in need thereof a therapeutically effective amount of a compound of formula (I) as defined above.

Another aspect of this invention is directed to a pharmaceutical composition useful in lowering plasma levels of Lp(a) in a human, which composition comprises an effective amount of a compound of formula (I) as defined above and a pharmaceutically acceptable excipient.

A further aspect of this invention is directed to a pharmaceutical composition useful in inhibiting the generation of apo(a) in a human, which composition comprises an effective amount of a compound of formula (I) as defined above and a pharmaceutically acceptable excipient.

Another aspect of this invention is directed to a method of inhibiting the generation of apo(a) in vitro or in vivo by administering a compound of formula (I) as defined above.

DETAILED DESCRIPTION OF THE INVENTION

Definitions

As used in the specification and appended claims, unless specified to the contrary, the following terms have the meaning indicated:

"Alkyl" refers to a straight or branched chain monovalent radical consisting solely of carbon and hydrogen atoms, containing no unsaturation and having from one to ten carbon atoms, e.g., methyl, ethyl, propyl, butyl, 1-methylethyl (iso-propyl), 1,1-dimethylethyl (tert-butyl), pentyl, n-hexyl, n-decyl, and the like.

"Alkoxy" refers to a radical of the formula —OR$_a$ where R$_a$ is alkyl as defined above, e.g., methoxy, ethoxy, n-propoxy, n-heptoxy, and the like.

"Premature occlusive arterial disease" refers to those disease-states, for the purposes of this invention, which are characterized by the progressive narrowing and eventual closure of an artery or the process of progressive narrowing and eventual closing an artery, and which a) develop earlier in life than normal and b) are associated with high levels of Lp(a) in the plasma; and includes, inter alia, arteriosclerosis, atherosclerosis, coronary artery disease, peripheral artery disease, myocardial infarction, stroke, restenosis and bypass graft stenosis.

"Effective amount" refers to that amount of a compound of formula (I) which, when administered to a human, is sufficient to lower the plasma level of Lp(a) or to inhibit the generation of apo(a).

"Therapeutically effective amount" refers to that amount of a compound of formula (I) which, when administered to a human in need thereof, is sufficient to effect treatment, as defined below, for disease-states alleviated by the reduction of plasma levels of Lp(a) or by the inhibition of the generation of apo(a). The amount of a compound of formula (I) which constitutes a "therapeutically effective amount" will vary depending on the compound, the disease-state and its severity, and the age of the human to be treated, but can be determined routinely by one of ordinary skill in the art having regard to his own knowledge and to this disclosure.

"Treating" or "treatment" as used herein cover the treatment of a disease-state in a human, which disease-state is alleviated by the reduction of plasma levels of Lp(a) or the inhibition of the generation of apo(a); and include:

(i) preventing the disease-state from occurring in a human, in particular, when such human is predisposed to the disease-state but has not yet been diagnosed as having it;

(ii) inhibiting the disease-state, i.e., arresting its development; or (iii) relieving the disease-state, i.e., causing regression of the disease-state.

BRIEF DESCRIPTION OF THE DRAWINGS

Various other objects, features and attendant advantages of the invention will be more fully appreciated as the same becomes better understood when considered in conjunction with the accompanying drawings wherein.

PREFERRED EMBODIMENTS

Figure 1:
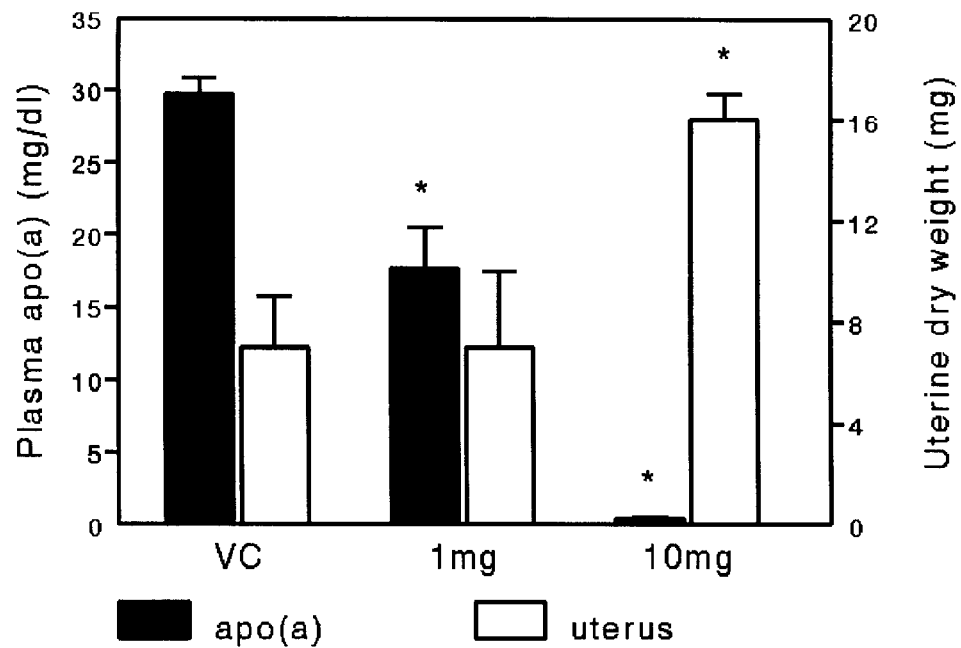
FIG. 1 shows plasma apo(a) levels and uterine dry weight of ovariectomized female apo(a) transgenic mice after treatment with either a compound of formula (I) or vehicle.

Of the various aspects of this invention as set forth above, a preferred aspect is the method of lowering plasma levels of Lp(a) in a human, which method comprises administering to a human in need thereof an effective amount of a compound of formula (I) of the following formula:

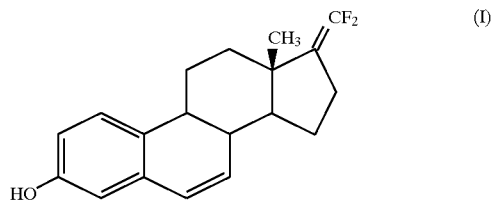

namely, 17-difluoromethlene-18-methylestra-1,3,5(10)-trien-3-ol.

Another preferred aspect of this invention is the method of inhibiting the generation of apo(a) in a human, which method comprises administering to a human in need thereof an effective amount of the compound of formula (I) as described above.

Another preferred aspect of this invention is the method of treating a human having a premature occlusive vascular disease which is alleviated by the reduction of plasma levels of Lp(a), which method comprises administering to the human in need thereof a therapeutically effective amount of the compound of formula (I) as described above.

Another preferred aspect of this invention is the method of treating a human having a premature occlusive vascular disease which is alleviated by the inhibition of the generation of apo(a), which method comprises administering to the human in need thereof a therapeutically effective amount of the compound of formula (I) as described above.

Utility of the Invention

This invention is directed to methods for lowering the plasma level of Lp(a) or for inhibiting the generation of apo(a) in humans, particularly in women without significant side effect on the endometrium. As discussed above, there is a direct correlation between high levels of Lp(a) and premature occlusive arterial disease. However, the exact physiological function of either apo(a) or Lp(a) is still being investigated. Apparently, even the near absence of Lp(a) from plasma does not cause a deficiency syndrome or any kind of disease. Also, Lp(a) and apo(a) are apparently absent in the plasma from most species evolutionarily below Old World monkeys. However, various pathological functions have recently been postulated for both Lp(a) and apo(a)

based on the results of certain in vitro and in vivo studies as indicators of premature occlusive arterial diseases.

For example, it is known that from the total pool of cholesterol that is transported in the blood, only a very small fraction is associated with Lp(a). This small pool, however, is believed to act as "quick response" reserve for areas where rapid cell turnover, active membrane biosynthesis or inflammatory processes occur, such as the atheromatous plaque. Indeed, high levels of Lp(a) have been found to be localized in the vascular intima (significantly more than the circulating plasma level would indicate), especially in the intima at sites of atheromatous lesions and stenotic saphenous vein bypass grafts.

Another proposed function involves the endothelium, which is normally antithrombogenic. The luminal surface of endothelial cells binds plasminogen, which is activated by tissue plasminogen activator (TPA) on the endothelial cell surface to produce the antithrombogenic agent, plasmin. It is postulated that Lp(a) binds competitively to the plasminogen binding site and reduces the amount of plasmin generated by TPA. This can lead to reduced antithrombogenic and antifibrinolytic properties of the endothelium.

It has also been shown that Lp(a) binds to fibrin, which may prevent degradation of an existing thrombus by plasminogen and may contribute to Lp(a) accumulation in atherosclerotic plaques.

It has also been shown that Lp(a) prolongs the time required for fibrinolysis in an assay where fibrinolytic activity is stimulated by a fibrinolytic agent, e.g., TPA/streptokinase. The mechanism for this appears to be an inhibition of the conversion of plasminogen to plasmin by the fibrinolytic agent. Further evidence for its potential role in atherosclerosis is provided by studies showing monocyte adhesion glycoprotein expression by endothelial cells as a result of treatment with Lp(a). In addition, a recent study showed that Lp(a) may contribute to activation of immune response in atheromatous lesions.

Recently, it has been shown that transgenic mice expressing the human apo(a) gene develop atherosclerotic lesions in response to a high fat diet, which suggests a causative link between atherogenesis and apo(a), a necessary component of Lp(a). See, Lawn, R. M. et al., *Nature* 1992, Vol. 360, pp. 670–672.

To demonstrate the utility of the compounds of the invention as therapeutic agents for treating disease-states which are alleviated by the reduction of plasma Lp(a) levels, we evaluated the compounds for their ability to inhibit the generation of apo(a) in mice made transgenic for the human apo(a) gene (see Frazer, K. A. et al., *Nature Genetics* (1995), Vol. 9, pp. 424–431, for description of the transgenic mice). In particular, the transgenic mice were treated with the compounds of the invention and their plasma levels of apo(a) were determined. In addition, the uterine dry weight of each mouse was determined to demonstrate any side effect of the treatment on the uterus.

As illustrated in FIG. 1, a significant decrease in the plasma apo(a) levels of the treated mice was observed. In addition, as illustrated in FIG. 1, the compounds appear to have little or no significant effect on the uterus, as evidenced by the uterine dry weight of the mice after treatment. Since apo(a) is a necessary component of Lp(a), a reduction in the level of apo(a) would also reduce the level of Lp(a) in the plasma. Compounds which reduce plasma levels of Lp(a) would, upon administration, alleviate those disease-states which are characterized by high levels of Lp(a), such as premature occlusive arterial diseases.

B. Preparation of the Compounds of the Invention

The compounds used in this invention are selected from the following formula (I):

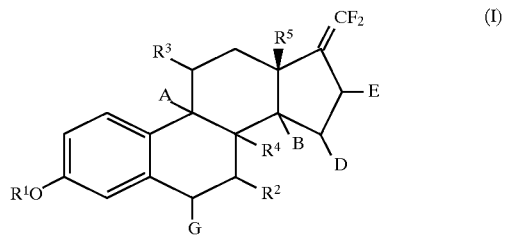

wherein:
R$^1$ is hydrogen or alkyl;
A, B, D, E, G, R$^2$ and R$^3$ each are hydrogen, and R$^4$ is hydrogen in the β-position; or
R$^2$ with R$^4$, R$^4$ with A, A with R$^3$, B with D, D with E, or G with R$^2$ is a bond, and the other substituents are each hydrogen; or
R$^2$ is alkyl in the β-position and A, B, D, E, G, R$^3$ and R$^4$ are each hydrogen; or
R$^3$ is alkoxy in the β-position and A, B, D, E, G, R$^2$ and R$^4$ are each hydrogen; or
R$^4$ is hydrogen in the α-position and A, B, D, E, G, R$^2$ and R$^3$ are each hydrogen; and
R$^5$ is methyl or ethyl.

These compounds are prepared treating the corresponding 17-oxo compound of the following formula:

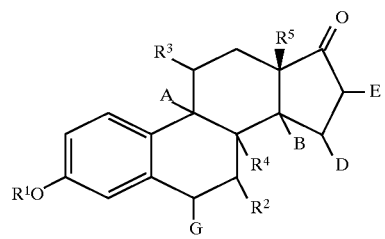

wherein R$^1$ is an hydroxy protecting group and A, B, D, E, G, R$^2$, R$^3$, R$^4$ and R$^5$ are the same as described above in the Summary of the Invention, with difluoromethyl-diphenylphosphine oxide or diethyl(difluoromethyl)phosphonate in the presence of a strong base in a aprotic solvent at a reflux temperature of from about 50° C. to about 100° C., and then optionally the 3-hydroxy protective group is cleaved under the action of an acid to produce the corresponding 3-hydroxy group, which can be optionally etherified.

The 3-hydroxy protective group is either a radical that can easily be cleaved in acid or basic environment, such as, for example, a tetrahydropyranyl (THP) group or a silyl group that is substituted with three identical, two identical, or three different straight or branched chain alkyl and/or aryl (such as phenyl or naphthyl) radicals, such as, for example, the trimethyl, t-butyldimethyl, methyldiphenyl, or t-butyldiphenylsilyl group or a methyl group, which can be removed, however, only under more drastic conditions.

Lithium diisopropylamide, sodium hydride, potassium t-butylate, butyllithium and the like are suitable as a strong base.

The reaction of the 17-oxo compound is carried out in an aprotic solvent, such as, for example, tetrahydrofuran, dimethyl sulfoxide, dimethylformamide, dioxane, or a mixture thereof.

The conditions for the cleavage of the 3-hydroxy protective group depends on its nature. Protective groups such as tetrahydropyranyl or a silyl radical can be removed under the action of a weak acid such as oxalic acid or an acidic ion exchanger, while the methyl group can be cleaved under the action of strong Lewis acids, e.g., dibutylaluminum hydride.

The etherification of the free 3-hydroxy group is carried out with a reagent that yields $R^1$ groups in a manner known to those skilled in the art.

The production of the 3-hydroxy-protected-17-oxo compounds used in the preparation of the compounds is carried out by reaction of the corresponding known 3-hydroxy compound with dihydropyran under the effect of para-toluenesulfonic acid in tetrhydrofuran or other methods known to those skilled in the art for protection of hydroxy groups.

Detailed synthesis of these compounds is described in detail in PCT Published Patent Application WO 96/28462 (Bohlmann et al.), which is incorporated in full by reference herein.

C. General Administration

Administration of the compounds of the invention, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the invention as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. Preferably, the composition will be about 5% to 75% by weight of a compound(s) of the invention, or a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of the invention, or a pharmaceutically acceptable salt thereof, is formed by the incorporation of any of the normally employed, pharmaceutically acceptable excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The compounds of the invention, or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of the invention (about 0.5% to about 20%), or a pharmaceutically acceptable salt thereof, and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, Ph buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences*, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state alleviated by the reduction of plasma levels of Lp(a) or by the inhibition of the generation of apo(a) in accordance with the teachings of this invention.

The compounds of the invention, or their pharmaceutically acceptable salts, are administered in a therapeutically effective amount which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disease-states; and the patient undergoing treatment. Generally, a therapeutically effective daily dose is from about 0.14 mg to about 14.3 mg/kg of body weight per day of a compound of the invention, or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, or a pharmaceutically acceptable salt thereof, preferably from about 50 mg to about 700 mg per day, and most preferably from about 100 mg to about 500 mg per day.

The following specific examples are provided as a guide to assist in the practice of the invention, and are not intended as a limitation on the scope of the invention.

EXAMPLE 1

Effect of a Compound of Formula (I) in Apo(a) Transgenic Mice

A. Ovariectomized female apo(a) transgenic mice were radomized into three groups, each group containing 3 animals. The test compound was 17-difluoromethylene-18-methylestra-1,3,5(10)-trien-3-ol. The mice were treated with daily subcutaneous injections of 1 mg/kg of the test compound in vehicle, 10 mg/kg of the test compound in vehicle, and vehicle (benzylbenzoate:castor oil, 1:9). Blood samples were collected via tail bleeding at the end of the first week and via heart puncture at the end of the second week of treatment when the mice were sacrificed. At sacrifice, the uteri of the animals were dissected, cleaned from adherent connnective tissues, place on aluminum foil and dried in an oven for 24 hours. At the time dry organ weight was determined. Apo(a) levels were determined from plasma using the Macra ELISA Kit (Stretegic Diagnostic).

Results of the study, as illustrated in FIG. 1, demonstrated that the test compound significantly lowered apo(a) levels at 1 mg/kg and 10 mg/kg dose, whereas significant uterotrophic activity (*p<0.05) was only measured at the 10 mg/kg dose. This dissociation in the efficacy of the test compound to lower apo(a) levels and increase uterine weight demonstrates the test compound feasibility as an apo(a)/Lp (a) lowering agent without significant side effects on the uterus.

EXAMPLE 2

This example illustrates the preparation of representative pharmaceutical compositions for oral administration containing a compound used in the invention, e.g., 17-difluoromethylene-18-methylestra-1,3,5(10)-trien-3-ol:

| A. | Ingredients | % wt./wt. |
| --- | --- | --- |
| | Compound of the invention | 20.0% |
| | Lactose | 79.5% |
| | Magnesium stearate | 0.5% |

The above ingredients are mixed and dispensed into hard-shell gelatin capsules containing 100 mg each.

| B. | Ingredients | % wt./wt. |
| --- | --- | --- |
| | Compound of the invention | 20.0% |
| | Magnesium stearate | 0.9% |
| | Starch | 8.6% |
| | Lactose | 69.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
| --- | --- | --- |
| | Compound of the invention | 0.1 g |
| | Propylene glycol | 20.0 g |
| | Polyethylene glycol 400 | 20.0 g |
| | Polysorbate 80 | 1.0 g |
| | Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. | Ingredients | % wt./wt. |
| --- | --- | --- |
| | Compound of the invention | 20.0% |
| | Peanut Oil | 78.0% |
| | Span 60 | 2.0% |

The above ingredients are melted, mixed and filled into soft elastic capsules.

| E. | Ingredients | % wt./wt. |
| --- | --- | --- |
| | Compound of the invention | 1.0% |
| | Methyl or carboxymethyl cellulose | 2.0% |
| | 0.9% saline | q.s. 100 mL |

The compound of the invention is dissolved in the cellulose/saline solution, filtered and bottled for use.

EXAMPLE 3

This Example illustrates the preparation of a representative pharmaceutical composition for parenteral administration containing a compound used in the invention, e.g., 17-difluoromethylene-18-methylestra-1,3,5(10)-trien-3-ol:

| Ingredients | |
| --- | --- |
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a $0.2\mu$ membrane filter and packaged under sterile conditions.

EXAMPLE 4

This Example illustrates the preparation of a representative pharmaceutical composition in suppository form containing a compound used in the invention, e.g., 17-difluoromethylene-18-methylestra-1,3,5(10)-trien-3-ol:

| Ingredients | % wt./wt. |
| --- | --- |
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 5

This Example illustrates the preparation of a representative pharmaceutical composition for insufflation containing a compound used in the invention, e.g., 17-difluoromethylene-18-methylestra-1,3,5(10)-trien-3-ol:

| Ingredients | % wt./wt. |
| --- | --- |
| Micronized compound of the invention | 1.0% |
| Micronized lactose | 99.0% |

The ingredients are milled, mixed, and packaged in an insufflator equipped with a dosing pump.

EXAMPLE 6

This Example illustrates the preparation of a representative pharmaceutical composition in nebulized form containing a compound used in the invention, e.g., 17-difluoromethylene-18-methylestra-1,3,5(10)-trien-3-ol:

| Ingredients | % wt./wt. |
| --- | --- |
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 7

This Example illustrates the preparation of a representative pharmaceutical composition in aerosol form containing a compound used in the invention, e.g., 17-difluoromethylene-18-methylestra-1,3,5(10)-trien-3-ol:

| Ingredients | % wt./wt. |
| --- | --- |
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of lowering plasma levels of Lp(a) in a human, which method comprises administering to the human in need thereof an effective amount of a compound of formula (I):

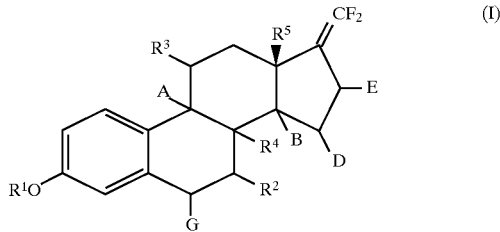

wherein:

$R^1$ is hydrogen or alkyl;

A, B, D, E, G, $R^2$ and $R^3$ each are hydrogen, and $R^4$ is hydrogen in the β-position; or $R^2$ with $R^4$, $R^4$ with A, A with $R^3$, B with D, D with E, or G with $R^2$ is a bond, and the other substituents are each hydrogen; or $R^2$ is alkyl in the β-position and A, B, D, E, G, $R^3$ and $R^4$ are each hydrogen; or $R^3$ is alkoxy in the β-position and A, B, D, E, G, $R^2$ and $R^4$ are each hydrogen; or $R^4$ is hydrogen in the α-position and A, B, D, E, G, $R^2$ and $R^3$ are each hydrogen; and $R^5$ is methyl or ethyl.

2. The method of claim 1 which comprises administering a compound of the formula:

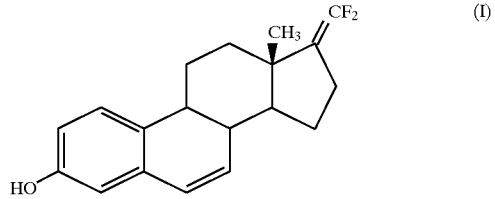

namely, 17-difluoromethylene-18-methylestra-1,3,5(10)-trien-3-ol.

3. A method of inhibiting the generation of apo(a) in a human, which method comprises administering a human in need thereof an effective amount of a compound of formula (I):

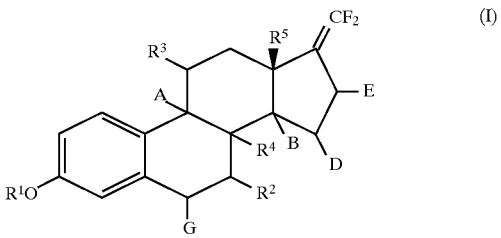

wherein:

$R^1$ is hydrogen or alkyl;

A, B, D, E, G, $R^2$ and $R^3$ each are hydrogen, and $R^4$ is hydrogen in the β-position; or $R^2$ with $R^4$, $R^4$ with A, A with $R^3$, B with D, D with E, or G with $R^2$ is a bond, and the other substituents are each hydrogen; or $R^2$ is alkyl in the β-position and A, B, D, E, G, $R^3$ and $R^4$ are each hydrogen; or $R^3$ is alkoxy in the β-position and A, B, D, E, G, $R^2$ and $R^4$ are each hydrogen; or $R^4$ is hydrogen in the α-position and A, B, D, E, G, $R^2$ and $R^3$ are each hydrogen; and $R^5$ is methyl or ethyl.

4. The method of claim 3 which comprises administering a compound of the formula:

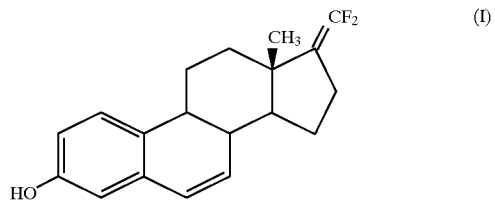

namely, 17-difluoromethylene-18-methylestra-1,3,5(10)-trien-3-ol.

5. A method of treating a disease-state which is alleviated by the reduction of plasma levels of Lp(a) in a human having said disease-state, wherein said disease-state is premature occlusive vascular disease, and wherein said method comprises administering to the human in need thereof a therapeutically effective amount of a compound of formula (I):

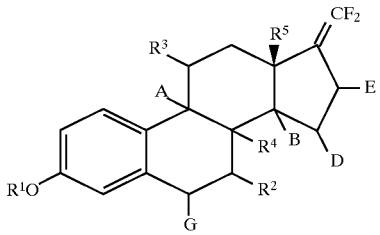

wherein:
R¹ is hydrogen or alkyl;
A, B, D, E, G, R² and R³ each are hydrogen, and R⁴ is hydrogen in the β-position; or
R² with R⁴, R⁴ with A, A with R³, B with D, D with E, or G with R² is a bond, and the other substituents are each hydrogen; or
R² is alkyl in the β-position and A, B, D, E, G, R³ and R⁴ are each hydrogen; or
R³ is alkoxy in the β-position and A, B, D, E, G, R² and R⁴ are each hydrogen; or
R⁴ is hydrogen in the α-position and A, B, D, E, G, R² and R³ are each hydrogen; and
R⁵ is methyl or ethyl.

6. The method of claim 5 which comprises administering a compound of the formula:

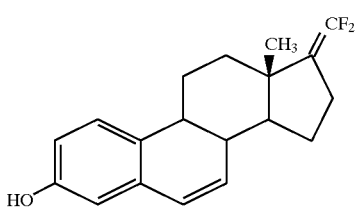

namely, 17-difluoromethylene-18-methylestra-1,3,5(10)-trien-3-ol.

7. The method of claim 5 wherein the disease-state is premature occlusive vascular disease and is stroke.

8. The method of claim 5 wherein the disease-state is premature occlusive vascular disease and is coronary heart disease.

9. The method of claim 5 wherein the disease-state is premature occlusive vascular disease and is diabetes mellitus.

10. The method of claim 5 wherein the disease-state is premature occlusive vascular disease and is atherosclerosis.

11. The method of claim 5 which comprises administering a compound of the formula:

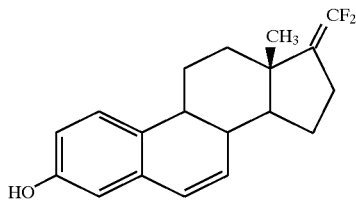

namely, 17-difluoromethylene-18-methylestra-1,3,5(10) trien-3-ol.

12. A method of treating a disease-state which is alleviated by the inhibition of generation of apo(a) in a human having said disease-state, wherein said disease-state is premature occlusive vascular disease, and wherein said method comprises administering to the human in need thereof a therapeutically effective amount of a compound of formula (I):

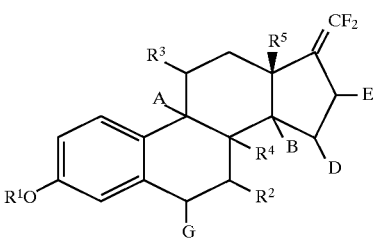

wherein:
R¹ is hydrogen or alkyl;
A, B, D, E, G, R² and R³ each are hydrogen, and R⁴ is hydrogen in the β-position; or
R² with R⁴, R⁴ with A, A with R³, B with D, D with E, or G with R² is a bond, and the other substituents are each hydrogen; or
R² is alkyl in the β-position and A, B, D, E, G, R³ and R⁴ are each hydrogen; or
R³ is alkoxy in the β-position and A, B, D, E, G, R² and R⁴ are each hydrogen; or
R⁴ is hydrogen in the α-position and A, B, D, E, G, R² and R³ are each hydrogen; and
R⁵ is methyl or ethyl.

13. The method of claim 12 which comprises administering a compound of the formula:

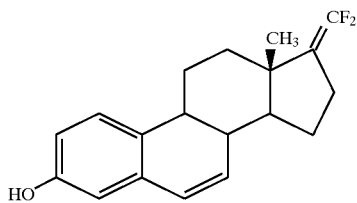

namely, 17-difluoromethylene-18-methylestra-1,3,5(10)-trien-3-ol.

14. The method of claim 12 wherein the disease-state is premature occlusive vascular disease and is stroke.

15. The method of claim 12 wherein the disease-state is premature occlusive vascular disease and is coronary heart disease.

16. The method of claim 12 wherein the disease-state is premature occlusive vascular disease and is diabetes mellitus.

17. The method of claim 12 wherein the disease-state is premature occlusive vascular disease and is atherosclerosis.

18. The method of claim 12 which comprises administering a compound of the formula:

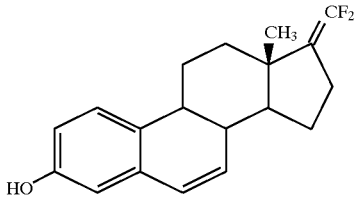

namely, 17-difluoromethylene-18methylestra-1,3,5(10)-trien-3ol.

19. A pharmaceutical composition useful in treating a human having a disease-state which is alleviated by the reduction of plasma levels of Lp(a), wherein said disease-state is premature occlusive vascular disease, and wherein said composition comprises a therapeutically effective amount of a compound of formula (I):

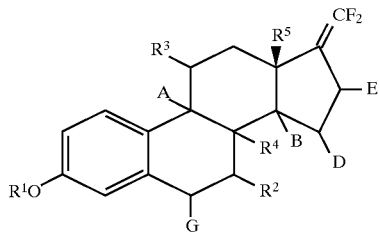

wherein:

R$^1$ is hydrogen or alkyl;

A, B, D, E, G, R$^2$ and R$^3$ each are hydrogen, and R$^4$ is hydrogen in the β-position; or R$^2$ with R$^4$, R$^4$ with A, A with R$^3$, B with D, D with E, or G with R$^2$ is a bond, and the other substituents are each hydrogen; or R$^2$ is alkyl in the β-position and A, B, D, E, G, R$^3$ and R$^4$ are each hydrogen; or R$^3$ is alkoxy in the β-position and A, B, D, E, G, R$^2$ and R$^4$ are each hydrogen; or R$^4$ is hydrogen in the α-position and A, B, D, E, G, R$^2$ and R$^3$ are each hydrogen; and R$^5$ is methyl or ethyl, and a pharmaceutically acceptable excipient.

20. The composition of claim 19 which comprises a therapeutically effective amount of a compound of the formula:

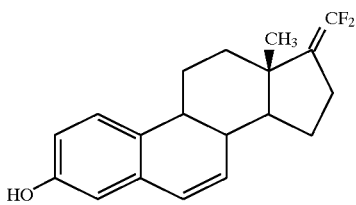

namely, 17-difluoromethylene-18-methylestra-1,3,5(10)-trien-3-ol.

21. A pharmaceutical composition useful in treating a human having a disease-state which is alleviated by the inhibition of the generation of apo(a), wherein said disease-state is premature occlusive vascular disease, and wherein said composition comprises a therapeutically effective amount of a compound of formula (I):

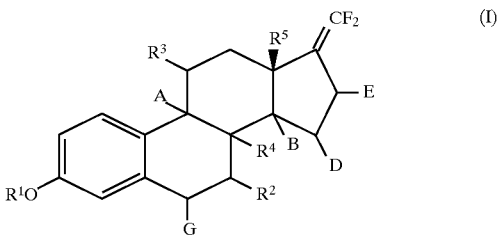

wherein:

R$^1$ is hydrogen or alkyl;

A, B, D, E, G, R$^2$ and R$^3$ each are hydrogen, and R$^4$ is hydrogen in the β-position; or R$^2$ with R$^4$, R$^4$ with A, A with R$^3$, B with D, D with E, or G with R$^2$ is a bond, and the other substituents are each hydrogen; or R$^2$ is alkyl in the β-position and A, B, D, E, G, R$^3$ and R$^4$ are each hydrogen; or R$^3$is alkoxy in the β-position and A, B, D, E, G, R$^2$ and R$^4$ are each hydrogen; or R$^4$ is hydrogen in the α-position and A, B, D, E, G, R$^2$ and R$^3$ are each hydrogen; and R$^5$ is methyl or ethyl, and a pharmaceutically acceptable excipient.

22. The composition of claim 21 which comprises a therapeutically effective amount of a compound of the formula:

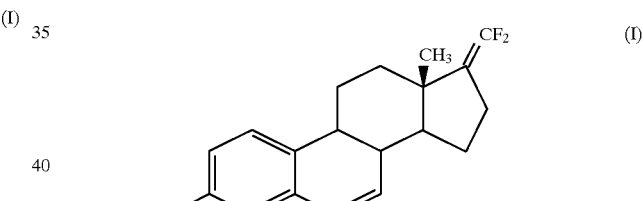

namely, 17-difluoromethylene-18-methylestra-1,3,5(10)-trien-3-ol.

* * * * *